United States Patent
Boernert et al.

(10) Patent No.: US 11,112,478 B2
(45) Date of Patent: Sep. 7, 2021

(54) SELECTION OF MAGNETIC RESONANCE FINGERPRINTING DICTIONARIES FOR ANATOMICAL REGIONS

(71) Applicant: KONINKLIJKE PHILIPS N.V., Eindhoven (NL)

(72) Inventors: Peter Boernert, Hamburg (DE); Thomas Erik Amthor, Hamburg (DE); Mariya Ivanova Doneva, Hamburg (DE); Fabian Wenzel, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 65 days.

(21) Appl. No.: 16/497,480

(22) PCT Filed: Mar. 30, 2018

(86) PCT No.: PCT/EP2018/058320
§ 371 (c)(1),
(2) Date: Sep. 25, 2019

(87) PCT Pub. No.: WO2018/178347
PCT Pub. Date: Oct. 4, 2018

(65) Prior Publication Data
US 2021/0109180 A1      Apr. 15, 2021

(30) Foreign Application Priority Data
Mar. 30, 2017   (EP) ..................................... 17163899

(51) Int. Cl.
*G01R 33/56* (2006.01)
*G01R 33/54* (2006.01)
(Continued)

(52) U.S. Cl.
CPC .......... *G01R 33/5608* (2013.01); *A61B 5/055* (2013.01); *G01R 33/246* (2013.01); *G01R 33/543* (2013.01)

(58) Field of Classification Search
CPC ................ G01R 33/50; G01R 33/4828; G01R 33/4625; G01R 33/5608; G01R 33/543;
(Continued)

(56) References Cited

U.S. PATENT DOCUMENTS

2010/0127704 A1    5/2010   Warntjes
2013/0265047 A1   10/2013  Griswold et al.
(Continued)

OTHER PUBLICATIONS

Ma et al "Magnetic Resonance Fingerprinting" Nature, vol. 495, pp. 187-193, Mar. 13, 2013.
(Continued)

*Primary Examiner* — Rishi R Patel

(57) ABSTRACT

The invention provides for a magnetic resonance imaging system (100) for acquiring MRF magnetic resonance data (144) from a subject (118) within a region of interest (109). The magnetic resonance imaging system comprises a processor (130) for controlling the magnetic resonance imaging system and a memory (134) for storing machine executable instructions (140) and MRF pulse sequence commands (142). The MRF pulse sequence commands are configured for controlling the magnetic resonance imaging system to acquire the MRF magnetic resonance data according to a magnetic resonance fingerprinting protocol. Execution of the machine executable instructions causes the processor to: acquire (200) the MRF magnetic resonance data for the region of interest by controlling the magnetic resonance imaging system with the MRF pulse sequence commands; receive (202) at least one magnetic resonance image (152) descriptive of the region of interest; identify (204) anatomical regions (156) within the region of interest using an
(Continued)

anatomical model (154); select (206) a local magnetic resonance fingerprinting dictionary (158) from a set of magnetic resonance fingerprinting dictionaries for each of the anatomical regions, wherein the local magnetic resonance fingerprinting dictionary comprises a listing of calculated MRF signals for a set of predetermined substances specific to each of the anatomical regions; and calculate (208) a composition mapping (160) of the predetermined substances for each of the anatomical regions using the MRF magnetic resonance data and the local magnetic resonance fingerprinting dictionary, wherein the composition mapping is a spatial average within each of the anatomical regions.

20 Claims, 5 Drawing Sheets

(51) Int. Cl.
   *G01R 33/24* (2006.01)
   *A61B 5/055* (2006.01)
(58) Field of Classification Search
   CPC .. G01R 33/246; A61B 5/055; G06K 2209/05; G06T 2207/10088
   See application file for complete search history.

(56) References Cited

U.S. PATENT DOCUMENTS

| | | |
|---|---|---|
| 2013/0271132 A1 | 10/2013 | Groswold |
| 2015/0301141 A1 | 10/2015 | Griswold et al. |
| 2015/0346301 A1 | 12/2015 | Cauley et al. |
| 2016/0282434 A1 | 9/2016 | Seiberlich et al. |
| 2016/0299206 A1 | 10/2016 | Cohen |
| 2016/0356871 A1 | 12/2016 | Grodzki |
| 2017/0106210 A1* | 4/2017 | Grodzki ............. G01R 33/4808 |
| 2018/0231626 A1* | 8/2018 | Gulani ................ A61B 5/4312 |

OTHER PUBLICATIONS

Gomez, P.A. et al "3D Magnetic Resonance Fingerprinting With a Clustered Spatiotemproal Dictionary" Proceedings of the International Soc. for Magnetic Resonance in Med. vol. 24, Apr. 22, 1016 p. 251.

Gomez, P.A. et al "Simultanous Parameter Mapping, Modality Synthesis, and Anatomical Labeling of the Brain With MR Fingerprinting" Network and Parallel Compting . . . p. 579-586 Oct. 2, 2016.

Hofmann et al "MRI Based Attenuation Correction for Whole Body PET/MRI Quantitative Evaluation of Segmentation and Atlas Based Methods" The Journal of Nuclear Medicine, vol. 52, No. 9, Aug. 9, 2011, p. 1392-1399.

Cocosco et al "A Fully Automatic and Robust Brain MRI Tissue Classification Method" Medical Imaging Anal, vol. 7, No. 4, Dec. 1, 2003 p. 513-527.

Gomez, P.A. et al "Learning a Spatiotemproal Dictionary for Magnetic Resonance Fingerprinting With Compressed Sensing" Netowrk and Parallel Computing, p. 112-119 Jan. 8, 2016.

Guo et al "MR Prostate Segmentation Via Distributed Discriminative Dictionary . . . " 2013 IEEE 10th International Symposium on Biomedical Imaging, vol. 10, April 7, 2013 p. 868-871.

Cauley et al "Fast Group Matching for MR Fingerprinting Reconstruction" Magnetic Resonance in MED. 74: p. 523-528 (2015.

\* cited by examiner

SELECTION OF MAGNETIC RESONANCE FINGERPRINTING DICTIONARIES FOR ANATOMICAL REGIONS

CROSS REFERENCE TO RELATED APPLICATIONS

This application is a U.S. national phase application of International Application No. PCT/EP2018/058320 filed on Mar. 30, 2018, which claims the benefit of EP Application Serial No. 17163899.2 filed on Mar. 30, 2017 and is incorporated herein by reference.

FIELD OF THE INVENTION

The invention relates to magnetic resonance imaging, in particular to magnetic resonance fingerprinting.

BACKGROUND OF THE INVENTION

Magnetic Resonance fingerprinting (MRF) is a technique where a number of RF pulses, distributed in time, are applied such that they cause signals from different materials or tissues to have a unique contribution to the measured Magnetic Resonance (MR) signal. A limited dictionary of precalculated signal contributions from a set or fixed number of substances is compared to the measured MR signals and within a single voxel the composition can be determined. For example if it is known that a voxel only contains water, fat, and muscle tissue the contribution from these three materials need only be considered and only a few RF pulses are needed to accurately determine the composition of the voxel.

The magnetic resonance fingerprinting technique was introduced in the journal article Ma et al., "Magnetic Resonance Fingerprinting," Nature, Vol. 495, pp. 187 to 193, doi:10.1038/nature11971. The magnetic fingerprinting technique is also described in United States patent applications US 2013/0271132 A1 and US 2013/0265047 A1.

SUMMARY OF THE INVENTION

The invention provides for a magnetic resonance imaging system, a computer program product, and a method in the independent claims. Embodiments are given in the dependent claims.

Embodiments may provide for a way of improving the specificity of the matching process in magnetic resonance fingerprinting. An anatomical model may be first matched or registered to a magnetic resonance image for a region of interest. The anatomical model is then used to select a local magnetic resonance fingerprinting dictionary for specific anatomical regions. Selecting a local magnetic resonance finger printing dictionary may have the benefit of eliminating substances or tissue types from the analysis that are not relevant for a particular anatomical region.

In one aspect, the invention provides for a magnetic resonance imaging system that may be adapted for acquiring magnetic resonance fingerprinting or MRF magnetic resonance data from a subject within a region of interest. The magnetic resonance imaging system comprises a processor for controlling the magnetic resonance imaging system. The magnetic resonance imaging system further comprises a memory for storing machine-executable instructions and pulse sequence commands. The MRF pulse sequence commands are configured for controlling the magnetic resonance imaging system to acquire the MRF magnetic resonance data according to a magnetic resonance fingerprinting protocol.

Execution of the machine-executable instructions causes the processor to acquire the MRF magnetic resonance data for the region of interest by controlling the magnetic resonance imaging system with the MRF pulse sequence commands. Execution of the machine-executable instructions further causes the processor to receive magnetic resonance data descriptive of the region of interest. These magnetic resonance data could for example be at least one magnetic resonance image. Alternatively, it could be the MRF magnetic resonance data or reconstructed MR fingerprints. For example MR fingerprints can be clustered. Clusters of MR fingerprints resulting from such clustering can be descriptive of the region of interest. Execution of the machine-executable instructions further cause the processor to identify anatomical regions within the region of interest using an anatomical model by registering the at least one magnetic resonance image or clustered MR fingerprints to the anatomical model. Execution of the machine-executable instructions further cause the processor to select a local magnetic resonance fingerprinting dictionary from a set of magnetic resonance fingerprinting dictionaries for each of the anatomical regions.

The local magnetic resonance fingerprinting dictionary comprises a listing of calculated MRF signals for a set of predetermined substances specific to each of the anatomical regions. Execution of the machine-executable instructions further cause the processor to calculate a composition mapping of the predetermined substances for each of the anatomical regions using the MRF magnetic resonance data and the local magnetic resonance fingerprinting dictionary. Preferably, first MR fingerprints are reconstructed from the MRF magnetic resonance data. The composition mapping is a spatial average within each of the anatomical regions.

This embodiment may be beneficial because the prior knowledge provided by the magnetic resonance image descriptive of the region of interest enables local magnetic resonance fingerprinting dictionaries to be selected before the magnetic resonance fingerprinting is conducted. This may enable more accurate determination of the composition of various anatomical regions.

The anatomical model may take different forms in different examples. In some cases it may be a deformable model which is then linked to a selection of the local magnetic resonance fingerprinting dictionaries for different regions of the deformable model. In other examples the anatomical model may take the form of an anatomical atlas which is then fit or registered to the at least one magnetic resonance image.

In some examples, the at least one magnetic resonance image is an image that is acquired prior, during or immediately after the MRF magnetic resonance data. The at least one magnetic resonance image may for example be a conventional magnetic resonance image or may be even images made from the MRF magnetic resonance data using a conventional magnetic resonance fingerprinting protocol.

In another embodiment, execution of the machine-executable instructions causes the spatial averaging to be performed by performing a voxel-by-voxel averaging of magnetic resonance fingerprints within each of the anatomical regions in image space before calculating the composition mapping using the local magnetic resonance fingerprinting dictionary.

Execution of the machine-executable instructions further cause the processor to perform the spatial averaging by performing a voxel-by-voxel averaging of the composition mapping after calculating the composition mapping using the local magnetic resonance fingerprinting dictionary. Execution of the machine-executable instructions further cause the spatial averaging to be performed by calculating the composition mapping using the local magnetic resonance fingerprinting dictionary such that the composition mapping provides the best fit to the voxels for each of the anatomical regions. This embodiment may have the benefit that it increases or improves the signal-to-noise greatly when calculating the composition mapping.

In some examples, when the spatial averaging is performed boundary regions between anatomical regions may be excluded. This may have the benefit of improving the spatial average within the anatomical regions.

In another embodiment, execution of the machine-executable instructions further causes the processor to determine a composition distribution for each voxel within an anatomical region selected from the anatomical regions. Execution of the machine-executable instructions further causes the processor to identify abnormal voxels within the anatomical region as abnormal if the composition distribution for the abnormal voxels differs from the spatial average within each of the anatomical regions by more than a predetermined threshold. This embodiment may be beneficial because the composition mapping for each of the anatomical regions is used to develop a baseline for what is considered to be normal for that particular anatomical region. Then the individual voxels within these anatomical regions can be compared to the composition distribution and it becomes very easy to identify abnormal regions within the anatomical regions. This may for example be useful in identifying regions automatically that may have abnormal tissue or composition.

The predetermined threshold could for example be an absolute value which is set or it could be a percentage change in a composition or in the composition.

In another embodiment, execution of the machine-executable instructions further causes the processor to determine an abnormal voxel composition for each of the abnormal voxels by using an abnormal tissue magnetic resonance fingerprinting dictionary according to the magnetic resonance fingerprinting dictionary. In this embodiment once the abnormal voxels have been identified the magnetic resonance fingerprinting can be performed again using a different magnetic resonance fingerprinting dictionary. For example when magnetic resonance fingerprinting is performed a larger number of predetermined substances or tissue types in the dictionary complicates the analysis. In this embodiment the particular anatomical region is first identified and then a local magnetic resonance fingerprinting dictionary is selected. Then abnormal voxels are identified and the abnormal voxels are then subjected to another round of magnetic resonance fingerprinting using yet again a different magnetic resonance fingerprinting dictionary. For example within particular anatomical regions there may be specific types of abnormal tissue or tumors which form. So the abnormal tissue magnetic resonance fingerprinting dictionary could also be specific to specific anatomical regions. This may provide for a greatly improved identification of abnormal tissue within anatomical regions.

In some embodiments, the identification of the abnormal voxels within boundary regions of composition maps is avoided. For example if there is a boundary between two anatomical regions it may be possible to detect the boundary and then to exempt voxels within a certain neighborhood of the boundary from the determination of the abnormal voxel composition.

In another embodiment, execution of the machine-executable instructions further cause the processor to identify boundary voxels between each of the anatomical regions. Execution of the machine-executable instructions further causes the processor to calculate partial voxel composition mappings for each of the boundary voxels using the local magnetic resonance fingerprinting dictionary for each anatomical region adjacent to each of the boundary voxels. In this embodiment a hybrid is used where it is understood that the boundary may contain tissue or compounds or constituents that belong to more than one type of anatomical region. In this example then the appropriate magnetic resonance fingerprinting dictionaries are selected so that the composition mapping of the boundary voxels is performed more accurately.

In another embodiment, execution of the machine-executable instructions further cause the processor to receive a B1+ mapping of the region of interest. Execution of the machine-executable instructions further causes the processor to correct the composition mapping using the B1+ mapping. This embodiment may be beneficial because the magnetic resonance fingerprinting technique provides a composition mapping which is spatially averaged within each of the anatomical regions. The B1+ field, the transmit RF field, may have spatial inhomogeneities due to the physical configuration of the magnetic resonance imaging system. This may provide for a means of correcting for the inhomogeneities in the B1+ field.

In another embodiment, the memory further contains B1+ mapping pulse sequence commands for acquiring B1+ mapping magnetic resonance data according to a B1+ mapping magnetic resonance imaging protocol. Execution of the machine-executable instructions further cause the processor to receive the B1+ mapping by acquiring the B1+ mapping magnetic resonance data by controlling the magnetic resonance imaging system with the B1+ mapping pulse sequence commands and then reconstructing the B1+ mapping using the B1+ mapping magnetic resonance data according to a B1+ mapping magnetic resonance imaging protocol.

The B1+ mapping MR protocol could for example be any method which is used to make a B1+ map. This may include, but does not exclude, the dual-angle method and the actual flip-angle imaging method. This may include several different phase-based methods such as the spin echo phase-sensitive or SEPS method, a compound excitation pulse with a gradient echo sequence to encode the flip-angle and the phase, or even the Bloch-Siegert shift method.

In another embodiment, execution of the machine-executable instructions further causes the processor to receive the B1+ map by reconstructing the B1+ map using the magnetic resonance data using a B1+ mapping magnetic resonance fingerprinting dictionary. The preliminary magnetic resonance fingerprinting dictionary comprises entries for B1+ mapping values. This embodiment may be beneficial because the process of performing a normal magnetic resonance fingerprinting of the region of interest may be used to develop the B1+ mapping also. It should be noted that the at least one magnetic resonance image could also be obtained using the MRF magnetic resonance data and applying a general magnetic resonance fingerprinting dictionary. In this case the same data could be used for generating the at least one magnetic resonance image which is then used to select the local magnetic resonance fingerprinting dictionaries and at the same time determine what the B1+ map is to further correct the accuracy of the spatial average within each of the anatomical regions for the composition mapping.

In another embodiment, the memory further comprises imaging pulse sequence commands according to an MR imaging protocol. The MR imaging protocol may be virtually any magnetic resonance imaging protocol which is used to develop an image which can then be fit to the anatomical model. This may include by does not exclude such things as the T1 map, a T2 map, or a proton density.

Execution of the machine-executable instructions further cause the processor to receive the at least one magnetic resonance image by acquiring the imaging magnetic resonance data by controlling the magnetic resonance imaging system with the imaging pulse sequence commands and then reconstructing the at least one magnetic resonance image from the imaging magnetic resonance data according to the MR imaging protocol.

In another embodiment, the anatomical model is any one of the following: a deformable model such as a deformable shape model and an anatomical atlas.

In another embodiment, the anatomical model comprises links between model regions identified and a selection of a local magnetic resonance fingerprinting dictionary from the set of magnetic resonance fingerprinting dictionaries.

In another aspect, the invention provides for a method of operating a magnetic resonance imaging system for acquiring MRF magnetic resonance data from a subject within a region of interest. The method comprises acquiring the MRF magnetic resonance data for the region of interest by controlling the magnetic resonance imaging system with pulse sequence commands. The MRF pulse sequence commands are configured for controlling the magnetic resonance imaging system to acquire the MRF magnetic resonance data according to a magnetic resonance fingerprinting protocol. The method further comprises receiving at least one magnetic resonance image descriptive of the region of interest.

The method further comprises identifying anatomical regions within the region of interest using an anatomical model. The method further comprises selecting a local magnetic resonance fingerprinting dictionary from a set of magnetic resonance fingerprinting dictionaries for each of the anatomical regions. The local magnetic resonance fingerprinting dictionary comprises a listing of calculated MRF signals for a set of predetermined substances specific to each of the anatomical regions. The method further comprises calculating a composition mapping of the predetermined substances for each of the anatomical regions using the MRF magnetic resonance data and the local magnetic resonance fingerprinting dictionary. The composition mapping is a spatial average within each of the anatomical regions.

In another embodiment, the spatial averaging is performed by performing a voxel-by-voxel averaging of the magnetic resonance fingerprints within each of the anatomical regions in image space before calculating the composition mapping using a local magnetic resonance fingerprinting dictionary.

In another embodiment, the spatial averaging is performed by doing a voxel-by-voxel averaging of the composition mapping after calculating the composition mapping using the local magnetic resonance fingerprinting dictionary.

In another embodiment, the spatial averaging is performed by calculating the composition mapping using the local magnetic resonance fingerprinting dictionary such that the composition mapping provides a best fit to all the voxels for each of the anatomical regions.

In another embodiment, the method further comprises determining a composition distribution for each voxel within an anatomical region selected from the anatomical regions.

The method further comprises identifying abnormal voxels within the anatomical region as abnormal if the composition distribution for the abnormal voxels differs from the spatial average within each of the anatomical regions by more than a predetermined threshold.

In another aspect, the invention provides for a computer program product comprising machine-executable instructions for execution by a processor controlling the magnetic resonance imaging system. Execution of the machine-executable instructions causes the processor to acquire the MRF magnetic resonance data for a region of interest by controlling the magnetic resonance imaging system with the MRF pulse sequence commands. The MRF pulse sequence commands are configured for controlling the magnetic resonance imaging system to acquire the MRF magnetic resonance data according to a magnetic resonance fingerprinting protocol. Execution of the machine-executable instructions further causes the processor to receive at least one magnetic resonance image descriptive of the region of interest. Execution of the machine-executable instructions further causes the processor to identify anatomical regions within the region of interest using an anatomical model. Execution of the machine-executable instructions further causes the processor to select a local magnetic resonance fingerprinting dictionary from a set of magnetic resonance fingerprinting dictionaries for each of the anatomical regions.

The local magnetic resonance fingerprinting dictionary comprises a listing of calculated MRF signals for a set of predetermined substances specific to each of the anatomical regions. Execution of the machine-executable instructions further causes the processor to calculate a composition mapping of the predetermined substances for each of the anatomical regions using the MRF magnetic resonance data and the local magnetic resonance fingerprinting dictionary. The composition mapping is a spatial average within each of the anatomical regions.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage may be any volatile or non-volatile computer-readable storage medium.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, bluetooth connection, wireless local area network connection, TCP/IP connection, ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) display, Electroluminescent display (ELD), Plasma display panel (PDP), Liquid crystal display (LCD), Organic light-emitting diode display (OLED), a projector, and Head-mounted display.

Magnetic Resonance (MR) data is defined herein as being the recorded measurements of radio frequency signals emitted by atomic spins using the antenna of a magnetic resonance apparatus during a magnetic resonance imaging scan. Preliminary magnetic resonance data is an example of medical imaging data. A Magnetic Resonance (MR) image is defined herein as being the reconstructed two or three dimensional visualization of anatomic data contained within the magnetic resonance imaging data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
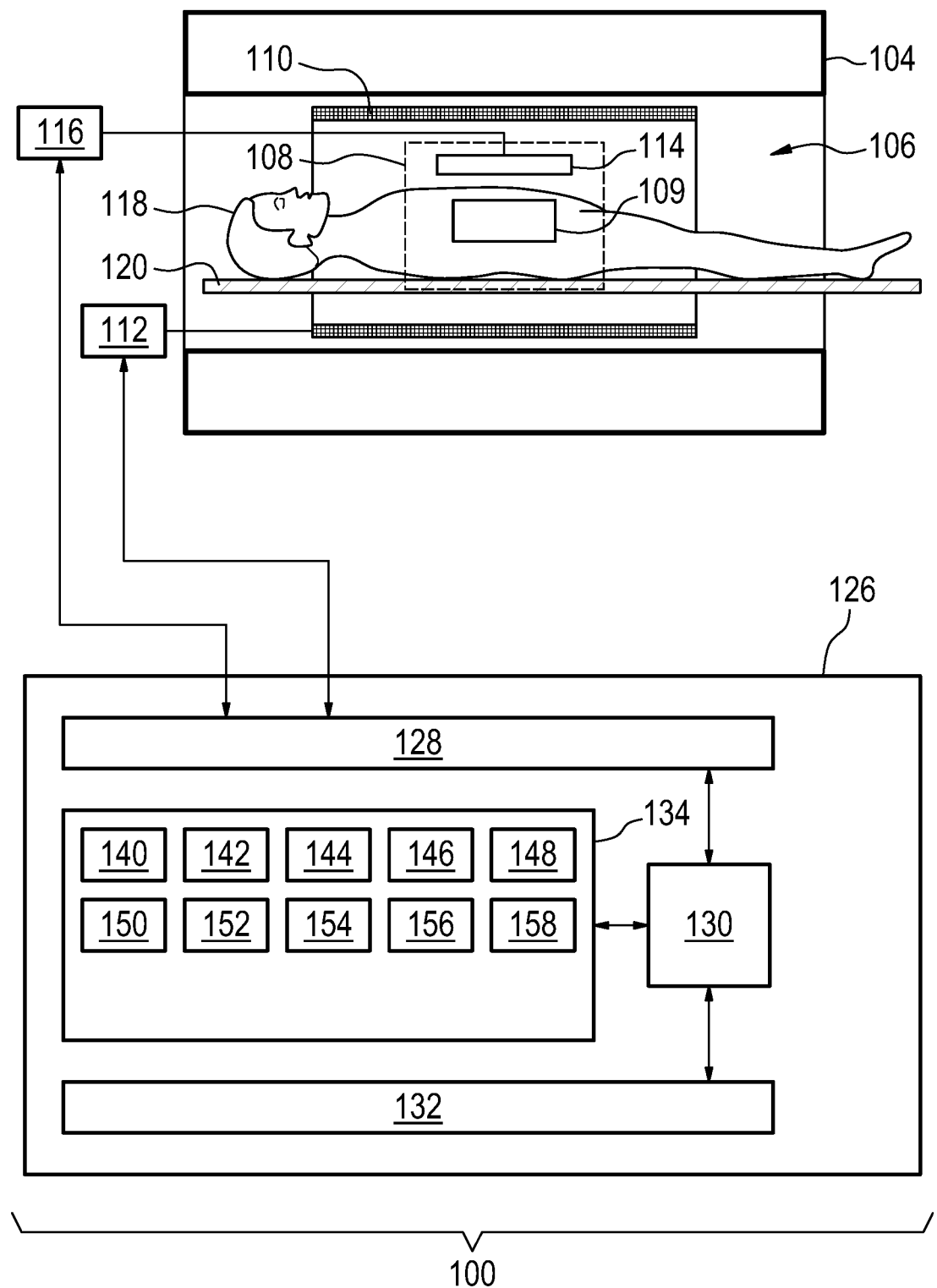
FIG. 1 illustrates an example of a magnetic resonance imaging system.

FIG. 1 shows an example of a magnetic resonance imaging system 100 with a magnet 104. The magnet 104 is a superconducting cylindrical type magnet with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of preliminary magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels. For example if a parallel imaging technique such as SENSE is performed, the radio-frequency could 114 will have multiple coil elements.

The transceiver 116 and the gradient controller 112 are shown as being connected to a hardware interface 128 of a computer system 126. The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 130 may be considered to be a non-transitory computer-readable medium.

The memory 134 is shown as containing machine-executable instructions 140 that enable the processor 130 to send and receive commands in order to control the operation and function of the magnetic resonance imaging system 100. The memory 134 is further shown as containing the MRF pulse sequence commands 142. The MRF pulse sequence commands are configured for acquiring MRF magnetic resonance data according to a magnetic resonance fingerprinting protocol.

The memory 134 is further shown as containing MRF magnetic resonance data that has been acquired by controlling the magnetic resonance imaging system 100 with the MRF pulse sequence commands 142. The MRF magnetic resonance data 144 is for the region of interest 109. The magnetic resonance data is repeatedly sampled after each repetition pulse of the MRF pulse sequence. These magnetic resonance data is then converted into a series of images. However, as the parameters used in the MRF pulse sequence may not be useful for imaging and also typically the data in Fourier space is under sampled. These series of images are then used to extract the data for each individual voxel and create a set of values or vector for the particular MRF pulse sequence commands. This series of values may be referred to as an MRF signal. The magnetic resonance fingerprinting dictionaries contain signals for particular substances or tissue types for the same MRF pulse sequence commands. The composition of an individual voxel can then be determined by comparing the measured MRF signal to the signals in the dictionary.

The memory 134 is shown as containing a number of intermediate images 146 that were repeated from repeatedly sampling the MRF magnetic resonance data 144. The computer memory 134 is shown as further containing an MRF signal 148 for a voxel constructed from the intermediate images 146. The computer memory 134 may also contain a B1+ mapping 150 and also possibly a B0 mapping which may be used to correct the intermediate images 146 before the MRF signal 148 is constructed.

The computer memory is further shown as containing a magnetic resonance image 152 which encompasses at least the region of interest 109. The computer memory 134 contains an anatomical model 154 which is used to generate a registration 156 of the magnetic resonance image 152. The registration 156 may be identification of various anatomical regions and/or also identification of what magnetic resonance fingerprinting dictionary to use within a particular anatomical region. The computer memory 134 is then shown as containing a local magnetic resonance fingerprinting dictionary 158 that was selected using the registration 156. The computer memory 134 is further shown as containing a composition mapping 160 that was constructed using the local magnetic resonance fingerprinting dictionary 158 and the MRF signal 148.

Figure 2:
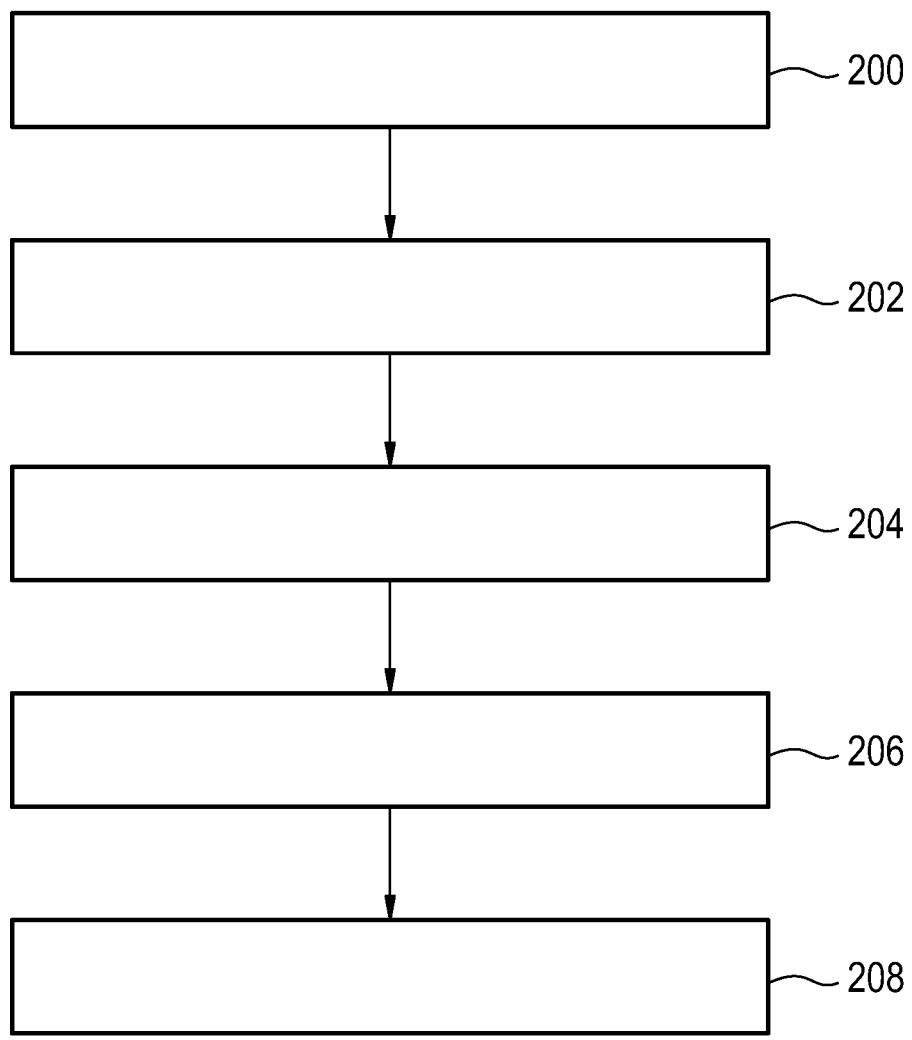
FIG. 2 shows a flow chart which illustrates a method of operating the magnetic resonance imaging system of FIG. 1.

FIG. 2 shows a flowchart which illustrates a method of operating the magnetic resonance imaging system 100 of FIG. 1. First in step 200 the MRF magnetic resonance data 144 is acquired by controlling the magnetic resonance imaging system 100 with the MRF pulse sequence commands 142. Next in step 202 the processor 130 receives the magnetic resonance image 152. This could be previously acquired or it could also be acquired by controlling the magnetic resonance imaging system to perform the imaging of the region of interest 109 before, after or during the magnetic resonance fingerprinting.

Next, in step 204 anatomical regions are identified to perform registration 156 using the magnetic resonance data 152 and the anatomical model 154. The magnetic resonance data could be the magnetic resonance image. Alternatively, The anatomical model is guided by the MRF data itself, to cluster voxels belonging to similar anatomical/functional structures. Next in step 206 the local magnetic resonance fingerprinting dictionary 158 is selected using the identification of the anatomical region 156. Finally, in step 208 the composition mapping 160 is calculated for a set of predetermined substances using the local magnetic resonance fingerprinting dictionary 158 and the MRF signal 148.

MR Fingerprinting (MRF) is a new and promising approach for tissue classification/characterization allowing to map quantitatively MR tissue parameters or tissue specific information to support future clinical diagnosis. In current MRF applications, the information from each voxel is analyzed individually, during the dictionary matching process. However, there is also spatially a correlation between the signals of individual voxels, which is not sufficiently used, yet. Voxels close to each other are likely to belong to the same tissue class or may be dominated by partial volumes of the same tissue.

Examples described herein may benefit from this correlation and to support also the diagnosing process, combining the usual dictionary evaluation with appropriate anatomical modeling. The anatomical model is guided by the MRF data itself, to cluster voxels belonging to similar anatomical/functional structures. In a second MRF matching step, the knowledge about the anatomical structures is then used to improve the specificity in the matching process. In this way, a structure specific tissue composition analysis is enabled (e.g. brain: white and gray matter, CSF and more), facilitating the identification of deviations and outliers, which could guide diagnoses in a very patient-specific manner.

The anatomical model could not only comprise the geometric extent of different organs or structures but also prior information about the most probable tissue type content/composition to be expected in the respective structure.

MRI has a great soft tissue contrast and is one of the most versatile imaging modalities. Quantitative MR techniques are desirable to reduce the huge variety of contrasts and/or to make findings more comparable to draw diagnostic conclusions. Quantitative MRI (qMRI) including the upcoming MR Fingerprinting (MRF) with its ability to give numbers is a very promising approach to identify important biomarkers that can ease diagnostics, therapy monitoring and follow up decisions.

Although MR Fingerprinting has great promise, the data evaluation/analysis process can be improved. Up to now, the signal of each voxel is analyzed individually, separated from the rest. However, there is lots of correlation among voxels. This applies especially to voxels that belong to the same tissue type, anatomy or functional structure. This correlation should be better used to improve future diagnosis or disease staging.

Examples may have one or more of the following features:
  expanded scope of the current dictionary based voxel signal matching process to more broader anatomical regions/compartments/functional structures using appropriate anatomical models which are adapted to the MRF data and thus to the patient itself.
  Increased SNR for more precise MRF matching, improving further the accuracy of tissue composition analysis (partial volume) restricting that to anatomical/functional structures to derive future disease specific markers.
  Examples may also be used to help steering a potential iterative reconstruction to compensate for spatial under-sampling artifacts using the information derived from the adapted model as a prior.

Examples may also support a model-driven anatomical/functional clustering approach can identify tissue deviations and outliers from the mean for each region. Thus, suspicious spots can be identified patient/specifically, comparing the clustered region/based information with the voxel-wise, spatially resolved MRF analysis.

An example method may contain one or more of the following steps:

1. Acquire MRF image data
2. Perform standard dictionary matching to find quantitative parameter maps of all parameters encoded in the signal (e.g., T1, T2)
3. Using this multi-parametric information, anatomical regions are identified by matching an anatomic model to the image data. The multi-parametric, quantitative, and perfectly co-registered nature of the MRF maps allows for very accurate matching of the anatomic model.
4. For each anatomic region, a new and dedicated MRF dictionary is created, based on a) prior knowledge about the tissue components to be expected for this region, b) empirical knowledge about the fingerprints found in the region by measurement, c) both.
5. The individual dedicated MRF dictionaries may be extended with information on the respective surrounding tissues, so that partial volume effects at the tissue borders can be correctly taken into account.
6. An additional MRF matching process is performed for each anatomic region, to identify tissue types, voxel compositions, and deviations from expected signals with high specificity.
7. The results of the refined MRF analysis, especially the information about unexpected tissue signals, are displayed to the user, preferably as a (colored) overlay image on either the anatomic model data or any parameter contrast data derived from the initial MRF matching procedure.

In a first example: An usual MRF sequence is executed as part of a brain examination. In this example, a T1-spoiled MRF approach is chosen, using a fixed and short TR, changing only the flip angles of the base sequence. The sequence starts with an inversion pulse to enhance T1 weighting. An under-sampled spiral is employed for the spatial encoding of the signals in each TR. The flip angles are changed as a function of time in a predefined manner (matched to the corresponding dictionary generation process). The spiral sampling pattern is changed slightly from TR to TR to spoil the spatial sampling coherence.

After the acquisition and the reconstruction of each under-sampled spiral (per TR), parts of these complex data (images) sampled in time are averaged. The number of actual images averaged is at least equal or a multiple of the under-sampling factor used in the measurements (this is not a hard pre-requisite but make data processing easier). In this way a couple of fully sampled images of the same slice can be generated, that might show significant image artifacts due to the non-stationary signal behavior caused by the MRF encoding. These images can be used to adapt the anatomical model to the actual patient's anatomy. The anatomical model will be adapted to these images using appropriately fitting and matching procedures. The anatomical model could be fitted to the MRF data (image). The anatomical models may be fitted to differently averaged subsets of the MRF data reflecting different contrasts.

In a further refinement of this, also the MRF sequence can appropriately be adapted to allow the formation of the above mentioned support images that reflect different contrasts at small artifact level.

In another refinement, one does without the formation of those images and does a normal MRF mapping. Based on the parameter maps (like T1, T2, MO, etc.) and some simple prior knowledge/rules tissue classification is done. The outcome of this classification can be used for model adaptation.

After fitting the model, the voxels from different anatomical/functional structures are grouped together and their corresponding MRF signals are spatially averaged forming one MRF signal, representative for this region. This procedure can become rather complex. Thus, basic averaging can be performed by magnitude or more preferable by appropriate complex operations, which might also incorporate the information about the receive coil sensitivities. In this way, the SNR of the resulting MRF signal is improved, which eases the subsequent matching process. This approach can be used at rather low field strength, but at high field strength, also the information about $B1^+$ inhomogeneity should be considered to avoid averaging MRF signal that were obtained under different transmit conditions. This information might come from a previously measured $B1^+$ field map or could be delivered from by the model as a good guess. Alternatively, the $B1^+$ information can also be derived from a first full voxel-wise MRF analysis, as described above to match the anatomical model, in which also the RF inhomogeneity is part of the dictionary. Based on this information signals from iso-$B1^+$ regions can be averaged as described above, to form a few partly averaged higher SNR MRF responses that have to be individually matched to the dictionary.

Based on this or these signals also a MRF compartment analysis could be performed to identify the partial volume signal contributions for the entire structure with higher accuracy that for an individual voxel. This fitting/matching process could further be supported by prior knowledge given in the annotated atlas (as white matter could contain parts of gray matter, CSF and more.) helping to guide the partial tissue analysis.

As one outcome of this model augmented analysis, a detailed report is conceivable, containing information about the size/volume and the tissue composition of different organs or organ sub-regions. In this way the information can be complemented and compared to prior knowledge and standards/clinical recommendations. This means the actual findings can be matched to clinical ground truth data, but also to the individual subject.

Example 2

Examples may also be applicable in the brain. Here such information is very useful for diagnosing different diseases, which are associated with volume and composition changes (e.g. neuro degenerative diseases).

After determining the main tissue components, a voxel specific normal MRF matching procedure can be triggered, if not done already, as usual in MRF. Also in this matching procedure, a least square problem can be solved identifying a few unknown intra-voxel components. This fitting procedure can benefit from the global, just acquired knowledge about the potential tissue composition this voxel belongs to, guiding/constraining the local matching process to improve the condition.

Figure 3:
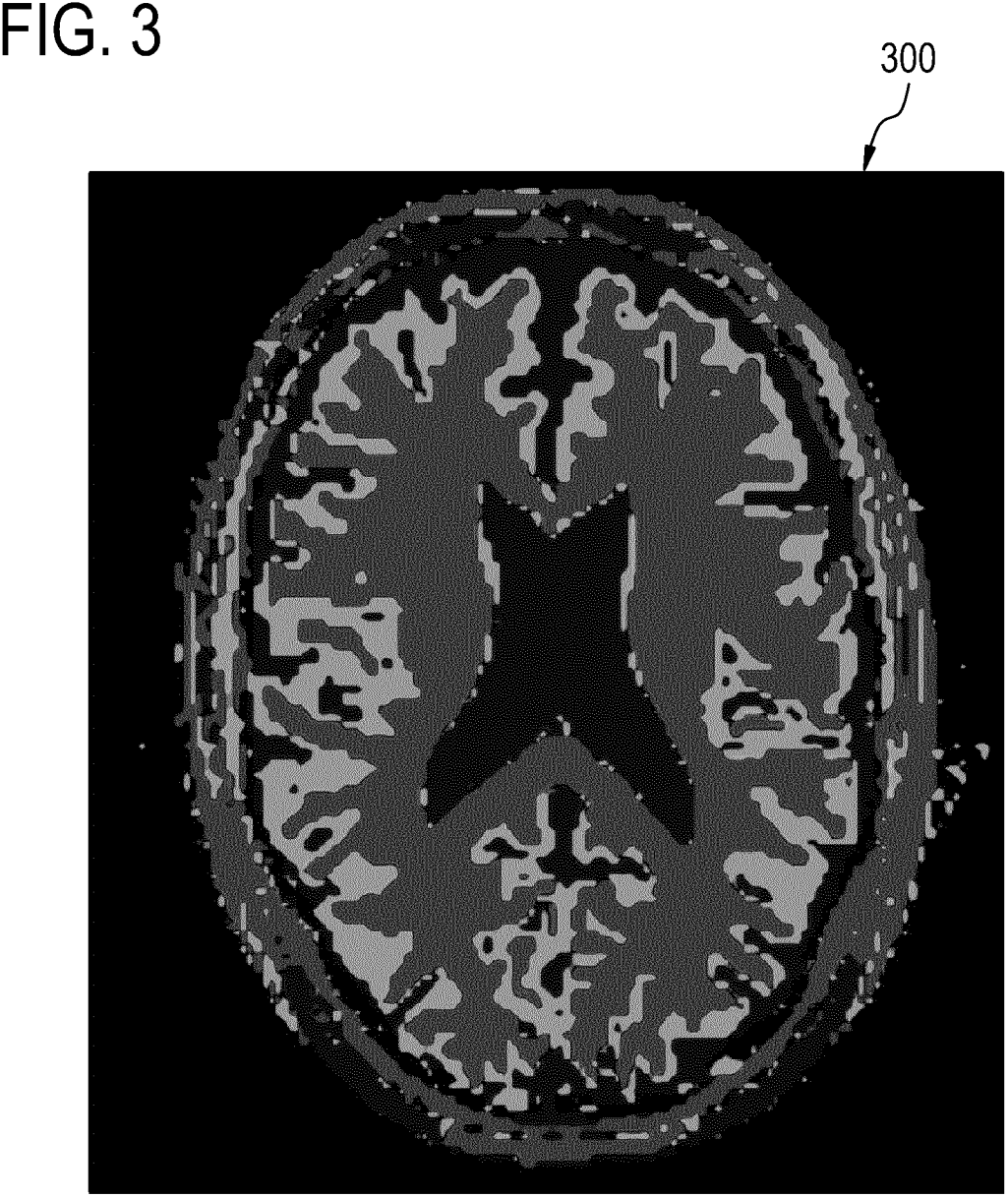
FIG. 3 shows an example of a MRF composition mapping or MRF image.
Figure 4:
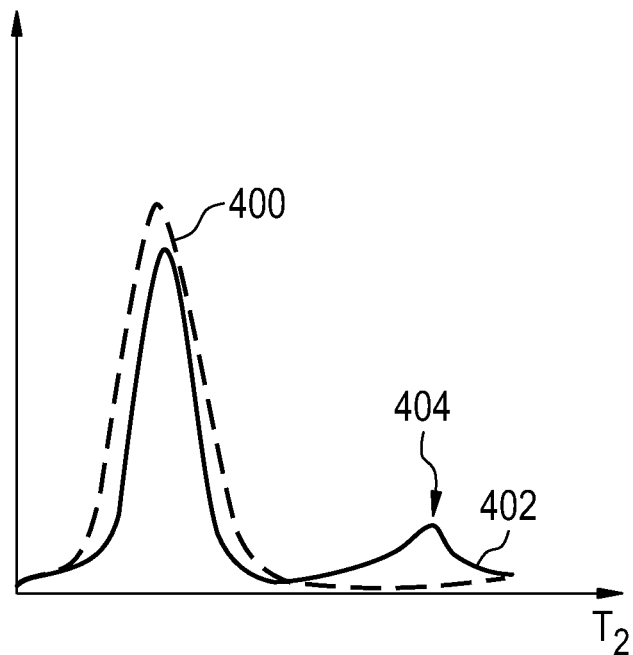
FIG. 4 shows expected and measured T2 distribution values within an anatomical region of FIG. 3.
Figure 5:
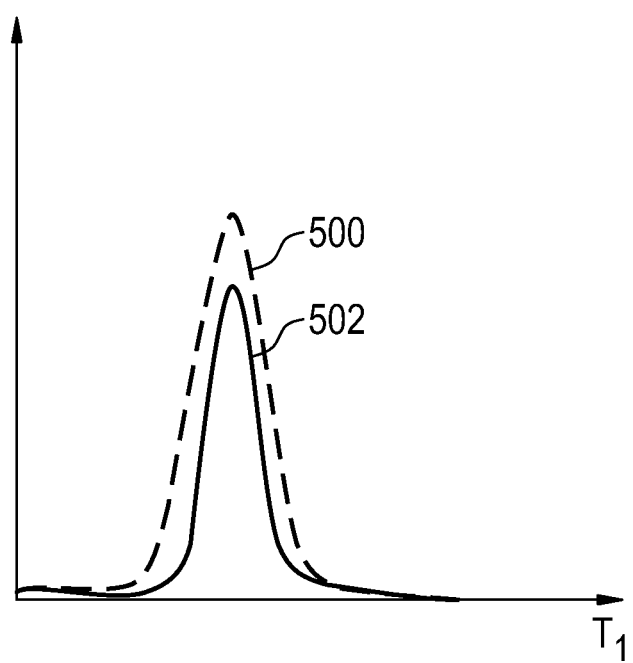
FIG. 5 shows expected and measured T1 distribution values within an anatomical region of FIG. 3.
Figure 6:
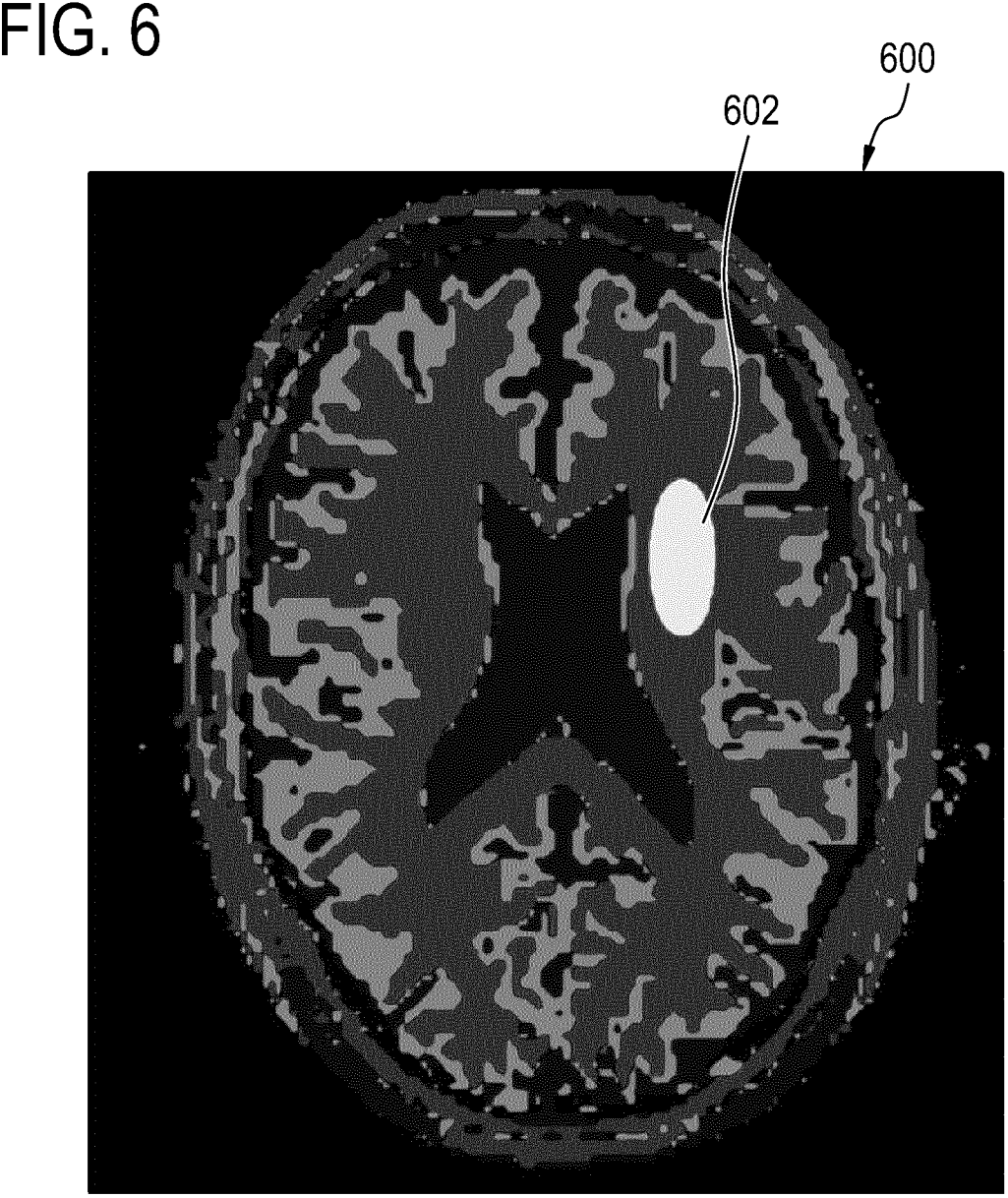
FIG. 6 shows a further example of a MRF composition mapping or MRF image.

FIGS. 3-6 are used to illustrate a method of detecting abnormal voxels and correcting them during magnetic resonance fingerprinting. It can be considered to be an anatomical model augmented outlier detection scheme. First in FIG. 3 is shown a composition mapping 300 or image from magnetic resonance fingerprinting. CSF, white, and gray matter are displayed in FIG. 3. FIG. 4 shows a T1 distribution 400 that could be expected within the white matter of the brain. The line 402 shows the actual measured T2 distribution for FIG. 3. It can be seen, that the region 404 of curve 402 is abnormal when compared to the curve 400. This may be used to identify voxels which are potentially abnormal. FIG. 5 shows a similar analysis for the T1 values. The curve 500 is the normal or expected T1 value for the white matter and 502 shows a distribution of measured values of T1. It can be seen that FIG. 4 and indicate some abnormalities. FIG. 6 shows a corrected MRF composition mapping 600. The abnormal voxels 602 have had their composition mapping recalculated using a new magnetic resonance fingerprinting dictionary. The voxels in region 602 are potentially abnormal and for example may indicate an abnormal tissue pathology.

In a third example: A similar set up like in example 1 was chosen, fitting the anatomical/functional models to the initial data. The information from the regional MRF responses, the resulting tissue composition and the entire anatomical model can be used as prior/constraint in an iterative reconstruction to reduce some of the aliasing in the individually sub-sampled time-domain images.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 magnet
106 bore of magnet
108 imaging zone
109 region of interest
110 magnetic field gradient coils
112 magnetic field gradient coil power supply
114 radio-frequency coil
116 transceiver
118 subject
120 subject support
126 computer system
128 hardware interface
130 processor
132 user interface
134 computer memory
140 machine executable instructions
142 MRF pulse sequence commands
144 MRF magnetic resonance data
146 intermediate images
148 MRF signal
150 B1+ mapping
152 magnetic resonance image
154 anatomical model
156 anatomical region or registration to model
158 local magnetic resonance fingerprinting dictionary
160 composition mapping
200 acquire the MRF magnetic resonance data for a region of interest by controlling the magnetic resonance imaging system with the MRF pulse sequence commands
202 receive at least one magnetic resonance image descriptive of the region of interest
204 identify anatomical regions within the region of interest using the anatomical model
206 select a local magnetic resonance fingerprinting dictionary from a set of magnetic resonance fingerprinting dictionaries for each of the anatomical regions
208 calculate a composition mapping of the predetermined substances for each of the anatomical regions using the MRF magnetic resonance data and the local magnetic resonance fingerprinting dictionary
300 MRF composition mapping or image
400 normal T2 distribution
402 measured T2 distribution
404 due to abnormal voxels
500 measured T1 distribution
502 measured T2 distribution
600 corrected MRF composition mapping or image
602 potential pathological structure

The invention claimed is:

1. A magnetic resonance imaging system for acquiring magnetic resonance fingerprinting (MRF) magnetic resonance data from a subject within a region of interest, wherein the magnetic resonance imaging system comprises:
a processor for controlling the magnetic resonance imaging system;
a memory for storing machine executable instructions and MRF pulse sequence commands, wherein the MRF pulse sequence commands are configured for controlling the magnetic resonance imaging system to acquire the MRF magnetic resonance data according to a magnetic resonance fingerprinting protocol,
wherein execution of the machine executable instructions causes the processor to:
acquire the MRF magnetic resonance data for the region of interest by controlling the magnetic resonance imaging system with the MRF pulse sequence commands and reconstruct MR fingerprints from the MRF magnetic resonance data;
receive magnetic resonance data descriptive of the region of interest;
identify anatomical regions within the region of interest in the magnetic resonance data using an anatomical model;
select a local magnetic resonance fingerprinting dictionary from a set of magnetic resonance fingerprinting dictionaries for each of the anatomical regions, wherein the local magnetic resonance fingerprinting dictionary comprises a listing of calculated MRF signals for a set of predetermined substances specific to each of the anatomical regions; and calculate a composition mapping of the predetermined substances for each of the anatomical regions using the MR fingerprints and the local magnetic resonance fingerprinting dictionary, wherein the composition mapping is a spatial average of voxels within each of the anatomical regions.

2. The medical imaging system of claim 1, wherein execution of the machine executable instructions causes the spatial averaging to be performed using any one of the following:

by performing a voxel by voxel averaging of the magnetic resonance fingerprints within each of the anatomical regions in image space before calculating the composition mapping using the local magnetic resonance fingerprinting dictionary;

by performing a voxel by voxel averaging of the composition mapping after calculating the composition mapping using the local magnetic resonance fingerprinting dictionary; and by calculating the composition mapping using the local magnetic resonance fingerprinting dictionary such that the composition mapping provides a best fit to the voxels for each of the anatomical regions.

3. The medical imaging system of claim 1, wherein execution of the machine executable instructions further causes the processor to:

determine a composition distribution for each voxel within an anatomical region selected from the anatomical regions; and identify abnormal voxels within the anatomical region as abnormal if the composition distribution for the abnormal voxels differs from the spatial average within each of the anatomical regions by more than a predetermined threshold.

4. The medical imaging system of claim 3, wherein execution of the machine executable instructions further causes the processor to determine an abnormal voxel composition for each of the abnormal voxels by using an abnormal tissue magnetic resonance fingerprinting dictionary according to the magnetic resonance fingerprinting dictionary.

5. The medical imaging system of claim 1, wherein execution of the machine executable instructions further causes the processor to:

identify boundary voxels between each of the anatomical regions;

calculate partial voxel composition mappings for each of the boundary voxels using the local magnetic resonance fingerprinting dictionary for each anatomical region adjacent to each of the boundary voxels.

6. The medical imaging system of claim 1, wherein execution of the machine executable instructions further causes the processor to receive a B1+ mapping of the region of interest, wherein execution of the machine executable instructions causes the processor to correct the composition mapping using the B1+ mapping.

7. The medical imaging system of claim 6, wherein the memory further contains B1+ mapping pulse sequence commands for acquiring B1+ mapping magnetic resonance data according to a B1+ mapping magnetic resonance imaging protocol, wherein execution of the machine executable instructions further causes the processor to receive the B1+ mapping by:

acquiring the B1+ mapping magnetic resonance data by controlling the magnetic resonance imaging system with the B1+ mapping pulse sequence commands; and reconstructing the B1+ mapping using the B1+ mapping magnetic resonance data according to a B1+ mapping magnetic resonance imaging protocol.

8. The medical imaging system of claim 6, wherein execution of the machine executable instructions causes the processor to receive the B1+ map by reconstructing the B1+ map using the MRF magnetic resonance data using a B1+ mapping magnetic resonance fingerprinting dictionary, wherein the B1+ mapping magnetic resonance fingerprinting dictionary comprises entries for B1+ mapping values.

9. The medical imaging system of claim 1, wherein the memory further comprises imaging pulse sequence commands according to an MR imaging protocol, wherein execution of the machine executable instructions further causes the processor to receive the at least one magnetic resonance image by:

acquiring the imaging magnetic resonance data by controlling the magnetic resonance imaging system with the imaging pulse sequence commands; and reconstructing the at least on magnetic resonance image from the imaging magnetic resonance data according to the MR imaging protocol.

10. The magnetic resonance imaging system of claim 1, wherein the anatomical model is any one of the following: a deformable model and an anatomical atlas.

11. The magnetic resonance imaging system of claim 1, wherein the anatomical model comprises links between model regions and a selection of the local magnetic resonance fingerprinting dictionary from the set of magnetic resonance fingerprinting dictionaries.

12. A method of operating a magnetic resonance imaging system for acquiring magnetic resonance fingerprinting (MRF) magnetic resonance data from a subject within a region of interest, wherein the method comprises:

acquiring the MRF magnetic resonance data for the region of interest by controlling the magnetic resonance imaging system with MRF pulse sequence commands, wherein the MRF pulse sequence commands are configured for controlling the magnetic resonance imaging system to acquire the MRF magnetic resonance data according to a magnetic resonance fingerprinting protocol and reconstructing MR fingerprints from the MRF magnetic resonance data;

receiving magnetic resonance data descriptive of the region of interest;

identifying anatomical regions within the region of interest in the magnetic resonance data using an anatomical model;

selecting a local magnetic resonance fingerprinting dictionary from a set of magnetic resonance fingerprinting dictionaries for each of the anatomical regions, wherein the local magnetic resonance fingerprinting dictionary comprises a listing of calculated MRF signals for a set of predetermined substances specific to each of the anatomical regions; and calculating a composition mapping of the predetermined substances for each of the anatomical regions using the MR fingerprints and the local magnetic resonance fingerprinting dictionary, wherein the composition mapping is a spatial average of voxels within each of the anatomical regions.

13. The method of claim 12, wherein the spatial averaging is performed using any one of the following:

by performing a voxel by voxel averaging of magnetic resonance fingerprints within each of the anatomical regions in image space before calculating the composition mapping using the local magnetic resonance fingerprinting dictionary;

by performing a voxel by voxel averaging of the composition mapping after calculating the composition mapping using the local magnetic resonance fingerprinting dictionary; and by calculating the composition mapping using the local magnetic resonance fingerprinting dictionary such that the composition mapping provides a best fit to the voxels for each of the anatomical regions.

14. The method of claim 12, wherein the method further comprises:

determining a composition distribution for each voxel within an anatomical region selected from the anatomical regions; and identifying abnormal voxels within the anatomical region as abnormal if the composition distribution for the abnormal voxels differs from the spatial average within each of the anatomical regions by more than a predetermined threshold.

15. A non-transitory computer readable medium storing machine executable instructions for execution by a processor controlling a magnetic resonance imaging system, wherein execution of the machine executable instructions causes the processor to:

acquire magnetic resonance fingerprinting (MRF) magnetic resonance data for a region of interest by controlling the magnetic resonance imaging system with MRF pulse sequence commands, wherein the MRF pulse sequence commands are configured for controlling the magnetic resonance imaging system to acquire the MRF magnetic resonance data according to a magnetic resonance fingerprinting protocol and reconstruct MR fingerprints from the MRF magnetic resonance data;

receive magnetic resonance data descriptive of the region of interest;

identify anatomical regions within the region of interest in the magnetic resonance data using an anatomical model;

select a local magnetic resonance fingerprinting dictionary from a set of magnetic resonance fingerprinting dictionaries for each of the anatomical regions, wherein the local magnetic resonance fingerprinting dictionary comprises a listing of calculated MRF signals for a set of predetermined substances specific to each of the anatomical regions; and calculate a composition mapping of the predetermined substances for each of the anatomical regions using the MR fingerprints and the local magnetic resonance fingerprinting dictionary, wherein the composition mapping is a spatial average of voxels within each of the anatomical regions.

16. The method of claim 14, further comprising:

determining an abnormal voxel composition for each of the abnormal voxels by using an abnormal tissue magnetic resonance fingerprinting dictionary according to the magnetic resonance fingerprinting dictionary.

17. The method of claim 12, further comprising:

identifying boundary voxels between each of the anatomical regions;

calculating partial voxel composition mappings for each of the boundary voxels using the local magnetic resonance fingerprinting dictionary for each anatomical region adjacent to each of the boundary voxels.

18. The non-transitory computer readable medium of claim 15, wherein execution of the machine executable instructions further causes the processor to:

determine a composition distribution for each voxel within an anatomical region selected from the anatomical regions; and identify abnormal voxels within the anatomical region as abnormal if the composition distribution for the abnormal voxels differs from the spatial average within each of the anatomical regions by more than a predetermined threshold.

19. The non-transitory computer readable medium of claim 18, wherein execution of the machine executable instructions further causes the processor to determine an abnormal voxel composition for each of the abnormal voxels by using an abnormal tissue magnetic resonance fingerprinting dictionary according to the magnetic resonance fingerprinting dictionary.

20. The non-transitory computer readable medium of claim 15, wherein execution of the machine executable instructions further causes the processor to:

identify boundary voxels between each of the anatomical regions;

calculate partial voxel composition mappings for each of the boundary voxels using the local magnetic resonance fingerprinting dictionary for each anatomical region adjacent to each of the boundary voxels.

* * * * *